（12） United States Patent
Sramek et al.

(10) Patent No.: US 10,932,691 B2
(45) Date of Patent: Mar. 2, 2021

(54) SURGICAL TOOLS HAVING ELECTROMAGNETIC TRACKING COMPONENTS

(71) Applicant: Auris Health, Inc., Redwood City, CA (US)

(72) Inventors: Christopher Sramek, Half Moon Bay, CA (US); Gregory J. Kintz, Santa Cruz, CA (US); Enrique Romo, Dublin, CA (US); Nahid Sidki, Great Falls, VA (US); Alan Yu, Union City, CA (US)

(73) Assignee: Auris Health, Inc., Redwood City, CA (US)

( * ) Notice: Subject to any disclaimer, the term of this patent is extended or adjusted under 35 U.S.C. 154(b) by 1010 days.

(21) Appl. No.: 15/411,562

(22) Filed: Jan. 20, 2017

(65) Prior Publication Data

US 2017/0209073 A1    Jul. 27, 2017

Related U.S. Application Data

(60) Provisional application No. 62/287,370, filed on Jan. 26, 2016.

(51) Int. Cl.
| *A61B 5/06* | (2006.01) |
| *A61B 1/005* | (2006.01) |
| *A61B 1/018* | (2006.01) |
| *A61B 34/20* | (2016.01) |
| *A61B 1/06* | (2006.01) |

(52) U.S. Cl.
CPC .............. *A61B 5/065* (2013.01); *A61B 1/005* (2013.01); *A61B 1/018* (2013.01); *A61B 1/0676* (2013.01); *A61B 2034/2051* (2016.02)

(58) Field of Classification Search
CPC .......... A61B 5/06; A61B 5/061; A61B 5/062; A61B 5/065; A61B 34/20; A61B 2034/2051
USPC .......................... 600/407, 424; 382/103, 128
See application file for complete search history.

(56) References Cited

U.S. PATENT DOCUMENTS

| 1,011,038 | A |   | 12/1911 | Davenport |
| 3,428,307 | A |   | 2/1969 | Owen |
| 3,620,210 | A |   | 11/1971 | Annas |
| 3,751,028 | A |   | 8/1973 | Scheininger |
| 4,173,228 | A | * | 11/1979 | Van Steenwyk ......... A61B 5/06 600/409 |
| 5,253,647 | A | * | 10/1993 | Takahashi .............. A61B 5/065 600/117 |
| 5,318,025 | A |   | 6/1994 | Dumoulin et al. |
| 5,429,132 | A | * | 7/1995 | Guy ........................ A61B 5/06 128/899 |
| 5,558,091 | A |   | 9/1996 | Acker et al. |

(Continued)

*Primary Examiner* — John R Downey
(74) *Attorney, Agent, or Firm* — Knobbe, Martens, Olson & Bear, LLP

(57) ABSTRACT

A surgical tool having an electromagnetic (EM) sensor component is provided. The surgical tool has a flexible shaft portion. Additionally, the surgical tool has a rigid portion attached to the flexible shaft portion. The rigid portion comprises at least one EM sensor within the rigid portion. The at least one EM sensor comprises an extended core portion surrounded by a coil. Additionally, the at least one EM sensor generates a change in voltage when exposed to an electromagnetic field.

27 Claims, 10 Drawing Sheets

(56) References Cited

U.S. PATENT DOCUMENTS

| | | | |
|---|---|---|---|
| 5,727,553 A * | 3/1998 | Saad | A61B 5/06 |
| | | | 128/899 |
| 5,913,168 A | 6/1999 | Moreau | |
| 6,004,271 A | 12/1999 | Moore | |
| 6,253,770 B1 * | 7/2001 | Acker | A61B 1/31 |
| | | | 128/899 |
| 6,310,573 B1 | 10/2001 | Samuelsson | |
| 6,530,913 B1 | 3/2003 | Giba et al. | |
| 6,544,230 B1 | 4/2003 | Flaherty | |
| 6,572,535 B2 * | 6/2003 | Watanabe | A61B 1/0055 |
| | | | 600/117 |
| 6,593,884 B1 * | 7/2003 | Gilboa | A61B 5/06 |
| | | | 342/448 |
| 6,610,007 B2 | 8/2003 | Belson et al. | |
| 6,636,757 B1 | 10/2003 | Jascob et al. | |
| 6,669,709 B1 | 12/2003 | Cohn | |
| 6,690,963 B2 * | 2/2004 | Ben-Haim | A61N 1/36564 |
| | | | 600/117 |
| 6,904,630 B2 | 6/2005 | Al-Kassim | |
| 6,905,460 B2 | 6/2005 | Wang et al. | |
| 6,944,492 B1 | 9/2005 | Persoons | |
| 7,371,210 B2 | 5/2008 | Brock | |
| 7,789,874 B2 | 9/2010 | Yu et al. | |
| 8,146,874 B2 | 4/2012 | Yu | |
| 8,302,221 B1 | 11/2012 | Camp, Jr. | |
| 8,505,137 B1 | 8/2013 | Gaines, Jr. | |
| 8,602,031 B2 | 12/2013 | Reis et al. | |
| 8,706,193 B2 * | 4/2014 | Govari | A61B 34/20 |
| | | | 600/424 |
| 8,720,448 B2 | 5/2014 | Reis et al. | |
| 8,827,948 B2 | 9/2014 | Romo et al. | |
| 8,894,610 B2 | 11/2014 | MacNamara et al. | |
| 8,932,207 B2 * | 1/2015 | Greenburg | A61B 1/0125 |
| | | | 600/117 |
| 8,961,533 B2 | 2/2015 | Stahler et al. | |
| 8,968,333 B2 | 3/2015 | Yu et al. | |
| 9,204,933 B2 | 12/2015 | Reis et al. | |
| 9,226,687 B2 | 1/2016 | Soper | |
| 9,254,123 B2 | 2/2016 | Alvarez et al. | |
| 9,301,726 B2 | 4/2016 | Mackie | |
| 9,314,306 B2 | 4/2016 | Yu | |
| 9,326,822 B2 | 5/2016 | Lewis et al. | |
| 9,408,669 B2 | 8/2016 | Kokish et al. | |
| 9,452,018 B2 | 9/2016 | Yu | |
| 9,504,604 B2 | 11/2016 | Alvarez | |
| 9,561,083 B2 | 2/2017 | Yu et al. | |
| 9,566,201 B2 | 2/2017 | Yu | |
| 9,622,827 B2 | 4/2017 | Yu et al. | |
| 9,636,184 B2 | 5/2017 | Lee et al. | |
| 9,713,509 B2 | 7/2017 | Schuh et al. | |
| 9,727,963 B2 | 8/2017 | Mintz et al. | |
| 9,737,371 B2 | 8/2017 | Romo et al. | |
| 9,737,373 B2 | 8/2017 | Schuh | |
| 9,744,335 B2 | 8/2017 | Jiang | |
| 9,763,741 B2 | 9/2017 | Alvarez et al. | |
| 9,788,910 B2 | 10/2017 | Schuh | |
| 9,818,681 B2 | 11/2017 | Machida | |
| 9,844,412 B2 | 12/2017 | Bogusky et al. | |
| 9,867,635 B2 | 1/2018 | Alvarez et al. | |
| 9,918,681 B2 | 3/2018 | Wallace et al. | |
| 9,931,025 B1 | 4/2018 | Graetzel et al. | |
| 9,949,749 B2 | 4/2018 | Noonan et al. | |
| 9,955,986 B2 | 5/2018 | Shah | |
| 9,962,228 B2 | 5/2018 | Schuh et al. | |
| 9,974,501 B2 * | 5/2018 | Hartmann | A61B 6/4405 |
| 10,016,900 B1 | 7/2018 | Meyer et al. | |
| 10,022,192 B1 | 7/2018 | Ummalaneni | |
| 10,136,959 B2 | 11/2018 | Mintz et al. | |
| 10,145,747 B1 | 12/2018 | Lin et al. | |
| 10,159,532 B1 | 12/2018 | Ummalaneni et al. | |
| 10,231,793 B2 | 3/2019 | Romo | |
| 10,244,926 B2 | 4/2019 | Noonan et al. | |
| 10,285,574 B2 | 5/2019 | Landey et al. | |
| 10,299,870 B2 | 5/2019 | Connolly et al. | |
| 10,426,559 B2 | 10/2019 | Graetzel et al. | |
| 10,434,660 B2 | 10/2019 | Meyer | |
| 10,464,209 B2 | 11/2019 | Ho et al. | |
| 10,470,830 B2 | 11/2019 | Hill | |
| 10,482,599 B2 | 11/2019 | Mintz et al. | |
| 10,517,692 B2 | 12/2019 | Eyre et al. | |
| 10,524,866 B2 | 1/2020 | Srinivasan | |
| 10,539,478 B2 | 1/2020 | Lin | |
| 10,543,048 B2 | 1/2020 | Noonan et al. | |
| 10,617,374 B2 | 4/2020 | Hartmann | |
| 10,639,114 B2 | 5/2020 | Schuh | |
| 10,646,279 B2 | 5/2020 | Tahmasebi Maraghoosh | |
| 10,677,910 B2 | 6/2020 | Reniers | |
| 10,702,346 B2 | 7/2020 | Popovic | |
| 10,722,140 B2 | 7/2020 | Izmirli | |
| 2001/0009976 A1 | 7/2001 | Panescu et al. | |
| 2001/0029366 A1 | 10/2001 | Swanson et al. | |
| 2001/0047133 A1 * | 11/2001 | Gilboa | A61B 5/06 |
| | | | 600/429 |
| 2002/0065455 A1 * | 5/2002 | Ben-Haim | A61N 1/36564 |
| | | | 600/407 |
| 2002/0087169 A1 | 7/2002 | Brock et al. | |
| 2002/0095730 A1 | 7/2002 | Al-Kassim | |
| 2002/0167313 A1 * | 11/2002 | Taimisto | A61B 5/062 |
| | | | 324/260 |
| 2002/0177789 A1 | 11/2002 | Ferry et al. | |
| 2003/0052785 A1 * | 3/2003 | Gisselberg | A61B 90/39 |
| | | | 340/572.8 |
| 2003/0074011 A1 | 4/2003 | Gilboa et al. | |
| 2003/0129750 A1 * | 7/2003 | Schwartz | A61B 5/042 |
| | | | 435/377 |
| 2003/0135204 A1 | 7/2003 | Lee et al. | |
| 2004/0162480 A1 | 8/2004 | Satragno | |
| 2004/0162487 A1 * | 8/2004 | Klingenbeck-Regn | A61B 5/0066 |
| | | | 600/427 |
| 2004/0172757 A1 | 9/2004 | Somasundaram | |
| 2004/0176751 A1 | 9/2004 | Weitzner et al. | |
| 2004/0193146 A1 | 9/2004 | Lee et al. | |
| 2004/0199072 A1 | 10/2004 | Sprouse et al. | |
| 2004/0220461 A1 * | 11/2004 | Schwartz | A61B 5/0422 |
| | | | 600/374 |
| 2005/0143944 A1 * | 6/2005 | Cech | B60R 21/0134 |
| | | | 702/115 |
| 2005/0182295 A1 | 8/2005 | Soper et al. | |
| 2005/0197767 A1 | 9/2005 | Nortrup | |
| 2006/0116571 A1 * | 6/2006 | Maschke | A61B 5/0066 |
| | | | 600/424 |
| 2006/0241397 A1 | 10/2006 | Govari | |
| 2007/0016007 A1 * | 1/2007 | Govari | A61B 5/0538 |
| | | | 600/424 |
| 2007/0025527 A1 | 2/2007 | Eichenseer | |
| 2007/0049797 A1 * | 3/2007 | Yoshida | A61B 1/00082 |
| | | | 600/117 |
| 2007/0060879 A1 | 3/2007 | Weitzner et al. | |
| 2007/0208252 A1 * | 9/2007 | Makower | A61B 6/037 |
| | | | 600/424 |
| 2007/0244388 A1 * | 10/2007 | Sato | A61B 1/00147 |
| | | | 600/424 |
| 2008/0300592 A1 | 12/2008 | Weitzner et al. | |
| 2009/0054884 A1 | 2/2009 | Farley et al. | |
| 2009/0064413 A1 | 3/2009 | Sliski | |
| 2009/0126113 A1 | 5/2009 | Hejkal et al. | |
| 2009/0139030 A1 | 6/2009 | Yang | |
| 2010/0016757 A1 * | 1/2010 | Greenburg | A61B 1/0125 |
| | | | 600/562 |
| 2010/0228191 A1 | 9/2010 | Alvarez et al. | |
| 2010/0319121 A1 | 12/2010 | Polomsky | |
| 2010/0324412 A1 * | 12/2010 | Govari | A61B 34/20 |
| | | | 600/424 |
| 2010/0331856 A1 | 12/2010 | Carlson et al. | |
| 2011/0066029 A1 * | 3/2011 | Lyu | A61M 25/0133 |
| | | | 600/424 |
| 2011/0152880 A1 | 6/2011 | Alvarez et al. | |
| 2012/0053453 A1 | 3/2012 | Graumann | |
| 2012/0158011 A1 | 6/2012 | Sandhu | |
| 2012/0172712 A1 | 7/2012 | Bar-Tal | |
| 2012/0174317 A1 | 7/2012 | Saracen | |

(56) References Cited

U.S. PATENT DOCUMENTS

| | | |
|---|---|---|
| 2013/0158346 A1 | 6/2013 | Soper |
| 2013/0162775 A1* | 6/2013 | Baumann ............... A61B 5/065 348/45 |
| 2013/0317519 A1 | 11/2013 | Romo et al. |
| 2014/0033432 A1 | 2/2014 | Marie |
| 2014/0069437 A1 | 3/2014 | Reis et al. |
| 2014/0142591 A1 | 5/2014 | Alvarez et al. |
| 2014/0276939 A1 | 9/2014 | Kokish et al. |
| 2014/0309649 A1 | 10/2014 | Alvarez et al. |
| 2014/0350387 A1 | 11/2014 | Siewerdsen et al. |
| 2014/0357984 A1 | 12/2014 | Wallace et al. |
| 2014/0364870 A1 | 12/2014 | Alvarez et al. |
| 2014/0379000 A1 | 12/2014 | Romo et al. |
| 2015/0026889 A1 | 1/2015 | Roselius |
| 2015/0047125 A1 | 2/2015 | Bae |
| 2015/0051592 A1 | 2/2015 | Kintz |
| 2015/0101442 A1 | 4/2015 | Romo |
| 2015/0119638 A1 | 4/2015 | Yu et al. |
| 2015/0164594 A1 | 6/2015 | Romo et al. |
| 2015/0164596 A1 | 6/2015 | Romo |
| 2015/0335480 A1 | 11/2015 | Alvarez et al. |
| 2016/0000627 A1 | 1/2016 | Jackson et al. |
| 2016/0001038 A1 | 1/2016 | Romo et al. |
| 2016/0151122 A1 | 6/2016 | Alvarez et al. |
| 2016/0270865 A1 | 9/2016 | Landey et al. |
| 2016/0287279 A1 | 10/2016 | Bovay et al. |
| 2016/0296294 A1 | 10/2016 | Moll et al. |
| 2016/0338783 A1 | 11/2016 | Romo et al. |
| 2016/0338785 A1 | 11/2016 | Kokish et al. |
| 2016/0374541 A1 | 12/2016 | Agrawal et al. |
| 2017/0007337 A1 | 1/2017 | Dan |
| 2017/0065364 A1 | 3/2017 | Schuh et al. |
| 2017/0065365 A1 | 3/2017 | Schuh |
| 2017/0100199 A1 | 4/2017 | Yu et al. |
| 2017/0105804 A1 | 4/2017 | Yu |
| 2017/0119413 A1 | 5/2017 | Romo |
| 2017/0119481 A1 | 5/2017 | Romo et al. |
| 2017/0165011 A1 | 6/2017 | Bovay et al. |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0215978 A1 | 8/2017 | Wallace et al. |
| 2017/0290631 A1 | 10/2017 | Lee et al. |
| 2017/0333679 A1 | 11/2017 | Jiang |
| 2017/0340396 A1 | 11/2017 | Romo et al. |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289431 A1 | 10/2018 | Draper et al. |
| 2018/0325499 A1 | 11/2018 | Landey et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000576 A1 | 1/2019 | Mintz et al. |
| 2019/0083183 A1 | 3/2019 | Moll et al. |
| 2019/0110839 A1 | 4/2019 | Rafii-Tari et al. |
| 2019/0110843 A1 | 4/2019 | Ummalaneni et al. |
| 2019/0151148 A1 | 4/2019 | Alvarez et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216576 A1 | 7/2019 | Eyre |
| 2019/0223974 A1 | 7/2019 | Romo |
| 2019/0228525 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda |
| 2019/0298465 A1 | 10/2019 | Chin |
| 2019/0328213 A1 | 10/2019 | Landey et al. |
| 2019/0336238 A1 | 11/2019 | Yu |
| 2019/0365201 A1 | 12/2019 | Noonan et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000530 A1 | 1/2020 | DeFonzo |
| 2020/0000533 A1 | 1/2020 | Schuh |
| 2020/0022767 A1 | 1/2020 | Hill |
| 2020/0038123 A1 | 2/2020 | Graetzel |
| 2020/0039086 A1 | 2/2020 | Meyer |
| 2020/0046434 A1 | 2/2020 | Graetzel |
| 2020/0054408 A1 | 2/2020 | Schuh et al. |
| 2020/0060516 A1 | 2/2020 | Baez |
| 2020/0085516 A1 | 3/2020 | DeFonzo |
| 2020/0093549 A1 | 3/2020 | Chin |
| 2020/0093554 A1 | 3/2020 | Schuh |
| 2020/0100845 A1 | 4/2020 | Julian |
| 2020/0100853 A1 | 4/2020 | Ho |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0146769 A1 | 5/2020 | Eyre |
| 2020/0170720 A1 | 6/2020 | Ummalaneni |
| 2020/0171660 A1 | 6/2020 | Ho |
| 2020/0188043 A1 | 6/2020 | Yu |
| 2020/0197112 A1 | 6/2020 | Chin |
| 2020/0206472 A1 | 7/2020 | Ma |
| 2020/0217733 A1 | 7/2020 | Lin |
| 2020/0222134 A1 | 7/2020 | Schuh |
| 2020/0237458 A1 | 7/2020 | DeFonzo |
| 2020/0261172 A1 | 8/2020 | Romo |
| 2020/0268459 A1 | 8/2020 | Noonan et al. |
| 2020/0268460 A1 | 8/2020 | Tse |
| 2020/0281787 A1 | 9/2020 | Ruiz |
| 2020/0297437 A1 | 9/2020 | Schuh |
| 2020/0305922 A1 | 10/2020 | Schuh |
| 2020/0305983 A1 | 10/2020 | Yampolsky |
| 2020/0305989 A1 | 10/2020 | Schuh |
| 2020/0315717 A1 | 10/2020 | Bovay |
| 2020/0315723 A1 | 10/2020 | Hassan |
| 2020/0323596 A1 | 10/2020 | Moll |
| 2020/0330167 A1 | 10/2020 | Romo |
| 2020/0345216 A1 | 11/2020 | Jenkins |

\* cited by examiner

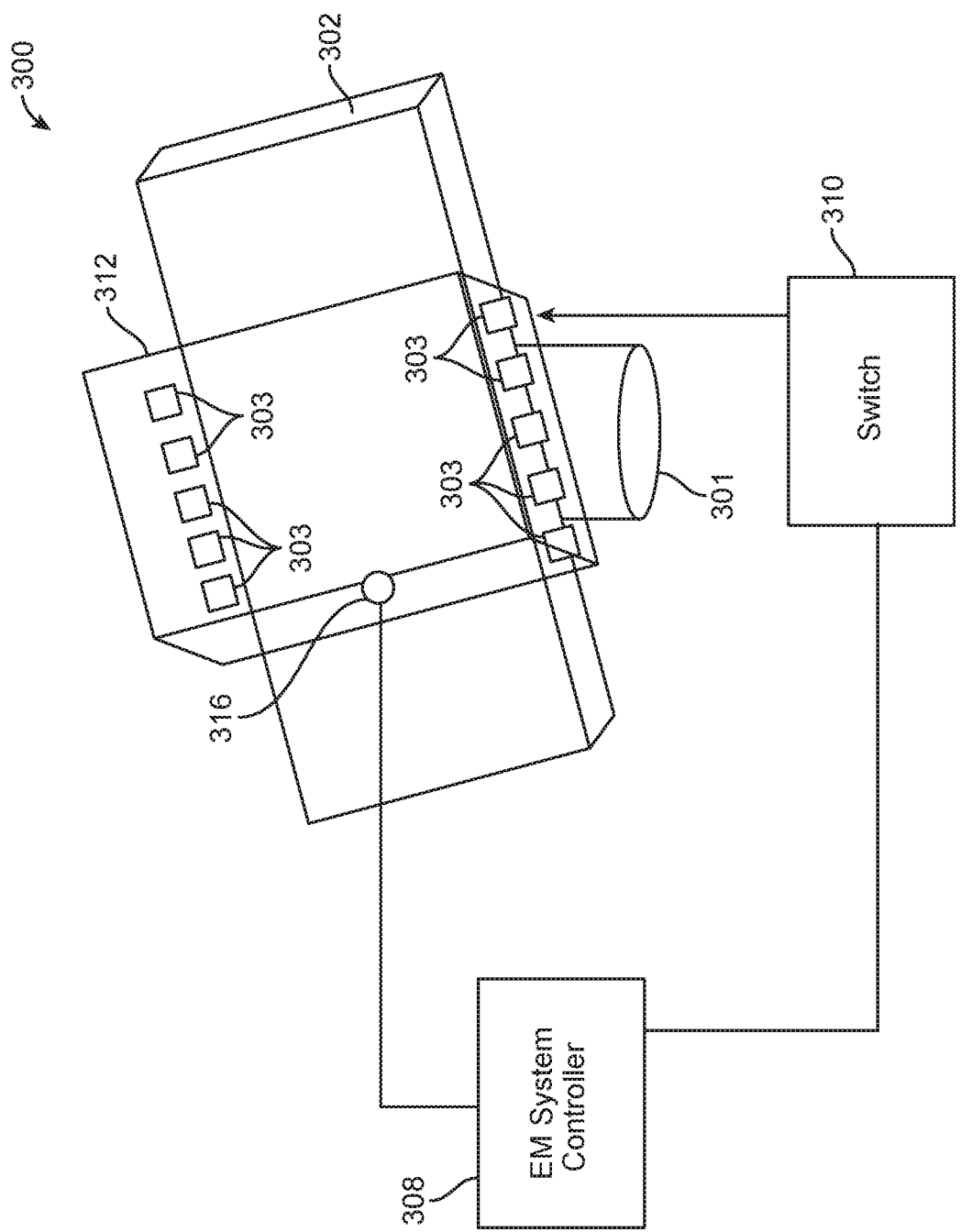

SURGICAL TOOLS HAVING ELECTROMAGNETIC TRACKING COMPONENTS

CROSS-REFERENCE TO RELATED APPLICATIONS

This application claims the benefit of U.S. Provisional Patent Application Ser. No. 62/287,370 entitled "Surgical Tools Having Electromagnetic Tracking Components," filed Jan. 26, 2016, the disclosure of which is hereby incorporated by reference in its entirety.

BACKGROUND

1. Field of the Invention

The field of the present application pertains to medical devices. More particularly, the field of the invention pertains to surgical tools having electromagnetic tracking components and methods of tracking the same.

2. Description of the Related Art

Surgical tools may be used to perform a surgical procedure on a patient. The surgical tools may include endoscopes, catheters, ureteroscopes, or other similar devices. Endoscopy is a widely-used, minimally invasive technique for both imaging and delivering therapeutics to anatomical locations within the human body. Typically a flexible endoscope is used to deliver tools to an operative site inside the body—e.g., through small incisions or a natural orifice in the body—where a surgical procedure is to be performed. Endoscopes may have imaging, lighting and steering capabilities at the distal end of a flexible shaft enabling navigation of non-linear lumens or pathways.

SUMMARY

In one aspect of the invention, surgical tools comprise one or more electromagnetic (EM) sensors that may be used to track placement and/or movement of the surgical tools during a surgical procedure. In examples, the surgical tools may interact with a field that is generated within an EM system for tracking of surgical tools. In particular, the one or more sensors associated with a surgical tool may be tracked based on interactions of the one or more sensors with an electromagnetic field.

Examples of surgical tools having EM sensors that may be used as tracking components may include endoscopes having one or more EM sensors disposed at the tip of the endoscope. In examples where an endoscope has two EM sensors, the EM sensors may be placed at oblique angles to one another so as provide additional orientation vectors (for example, but not limited to, roll, pitch, and yaw) that may be determined by comparing interactions of each EM sensor with an electromagnetic field. In additional examples, a surgical tool having one or more EM sensors may include an inwardly extended core so as to enhance sensor sensitivity. In further examples, a surgical tool having one or more EM sensors may include an outwardly extended core for sensing of force and/or mechanical palpitations.

Additional examples of surgical tools having EM sensors that may be used as tracking components may include catheters having a plurality of EM sensors placed along the length of the surgical tool. In particular, EM sensors may be placed at predetermined distances along a surgical tool so as to allow the tracking of a portion of the length of the surgical tool within a patient. By tracking a portion of the length of the surgical tool within a patient, the orientation of the surgical tool may be determined. In particular, sensors placed along a length of the surgical tool may be used to detect the changing shape of the surgical tool as it moves, such as when a catheter moves within a patient during surgery.

In one aspect of the invention, a surgical tool having an electromagnetic (EM) sensor component is provided. The surgical tool comprises a flexible shaft portion. Additionally, the surgical tool comprises a rigid portion attached to the flexible shaft portion. The rigid portion comprises at least one EM sensor within the rigid portion. Additionally, the at least one EM sensor comprises an extended core portion surrounded by a coil. Further, the at least one EM sensor generates a change in voltage when exposed to an electromagnetic field.

In another aspect of the invention, a surgical tool having an electromagnetic (EM) sensor component is provided. The surgical tool comprises a flexible shaft portion. Additionally, the surgical tool comprises a rigid portion attached to the flexible shaft portion. The rigid portion comprises two EM sensors within the rigid portion. Additionally, at least one EM sensor of the two EM sensors comprises an extended core portion surrounded by a coil.

In a further aspect of the invention, an electromagnetic (EM) system for tracking a surgical tool having at least one EM sensor integrated therein is provided. The EM system comprises a plurality of field generator coils disposed within a surgical bed, wherein the field generator coils are configured to generate an electromagnetic field within a control volume. Additionally, the EM system comprises an EM system controller configured to activate the field generator coils to generate the electromagnetic field within the control volume. The EM system also comprises at least one EM sensor integrated within a surgical tool, wherein the at least one EM sensor has an extended core, and wherein the at least one EM sensor is configured to generate a sensor signal in response to the electromagnetic field when the at least one EM sensor is located inside the control volume.

In an additional aspect of the invention, another surgical tool having an electromagnetic (EM) sensor component is provided. The surgical tool comprises a flexible shaft portion. Additionally, the surgical tool comprises a plurality of EM sensors positioned along the flexible shaft portion. The plurality of EM sensors are placed with a predetermined distance between successive EM sensors. Additionally, each EM sensor of the plurality of EM sensors comprises a core portion surrounded by a coil. At least one EM sensor of the plurality of EM sensors has a force sensing component. Further, each EM sensor of the plurality of EM sensors generates a change in voltage when exposed to an electromagnetic field.

It shall be understood that different aspects of the invention can be appreciated individually, collectively, or in combination with each other. Other objects and features of the present invention will become apparent by a review of the specification, claims, and appended figures.

BRIEF DESCRIPTION OF THE DRAWINGS

The invention will be described, by way of example, and with reference to the accompanying drawings, in which:

FIG. 3 illustrates a schematic of an EM tracking surgical system, in accordance with some embodiments;

DETAILED DESCRIPTION

Although certain preferred embodiments and examples are disclosed below, the inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

1. Integrating EM Sensors with Surgical Tools

Surgical tools having one or more EM sensors may be provided. In some examples, EM sensors may be embedded within surgical tools. In some examples, EM sensors may be integrated with surgical tools. In some examples, EM sensors may be coupled to one or more external portions of surgical tools.

Figure 1:
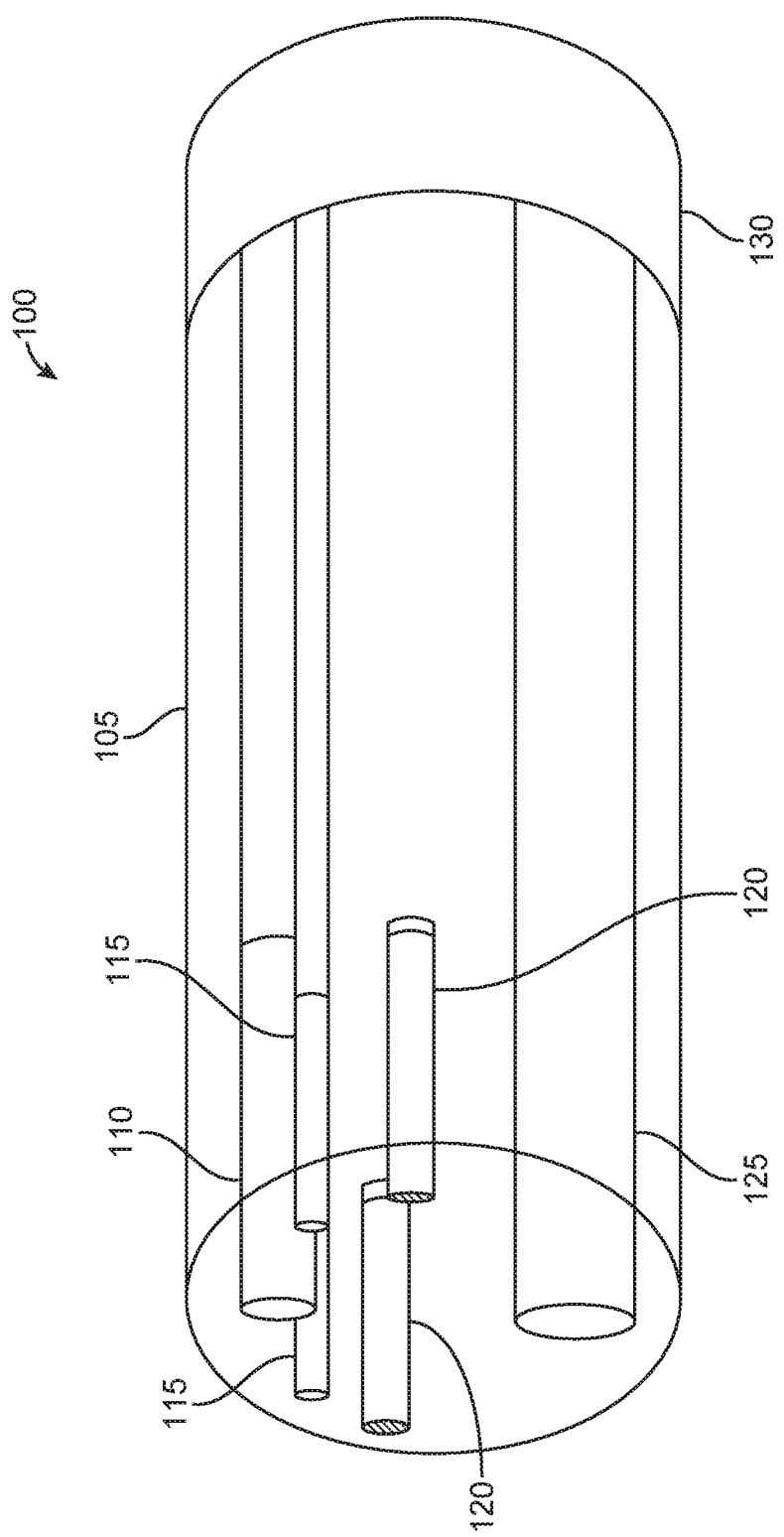
FIG. 1 illustrates a perspective view of an internal cross-section of an endoscope having electromagnetic (EM) sensors, in accordance with some embodiments.

Surgical tools as discussed herein may include endoscopes, catheters, ureteroscopes, or other similar devices. Accordingly, FIG. 1 illustrates a perspective view 100 of an internal cross-section of an endoscope having electromagnetic (EM) sensors 120, in accordance with some embodiments. As seen in FIG. 1, the internal cross-section of the endoscope comprises a rigid portion 105 and a flexible portion 130. The rigid portion 105 may comprise a tip of the endoscope. In examples, the EM sensors 120 within the endoscope may be used to spatially track the tip of the endoscope. Additionally, the flexible portion 130 may form part of a shaft of the endoscope. The flexible portion 130 may be operable connected to a robotic arm. In examples, endoscope that is partially illustrated in FIG. 1 may be used in conjunction with a robotic arm to assist in surgery of a patient.

The rigid portion 105 of an endoscope may include a camera 110, illumination sources 115, and a channel 125 for holding various surgical tools. Examples of illumination sources 115 may include fiber optics-illumination sources. Additionally, as seen in FIG. 1, the rigid portion may include a pair of EM sensors 120 that may be used as tracking components. In particular, the EM sensors 120 may be used for tracking a position of the rigid portion 105. Each EM sensor 120 may be surrounded by coils that may interact with an EM field that is generated by field generator coils. In examples, the system provided may be used for alternating current (AC) EM tracking. In other examples, the system may be used for direct current (DC) EM tracking. In examples, an EM sensor associated with a surgical tool may be tracked when voltage is induced within a sensor coil that is placed within the electromagnetic field. In examples, the system provided may be used for alternating current (AC) EM tracking. In other examples, the system may be used for direct current (DC) EM tracking. As the EM sensors 120 interact with the EM field, the EM sensors 120 may output voltage information which is related to a change in the EM field as the position and/or orientation of the EM sensors 120 changes. The change in the position and/or orientation of the EM sensors 120, in turn, may be associated with the change in the location of the rigid portion 105 of the surgical tool that contains the EM sensors 120. Small variations in position can be detected based on the interaction of EM sensors 120 with the EM field. The positional variations can have a spatial resolution of less than about 10 mm, 9 mm, 8 mm, 7 mm, 6 mm, 5 mm, 4 mm, 3 mm, 2 mm, or 1 mm. In some cases, the spatial resolution may be greater than about 10 mm.

In additional examples, the position of the endoscope may be determined based on input from the EM sensors 120 as well as input from camera 110. In particular, an initial position of the rigid portion 105 of the surgical tool may be determined based on interactions of the EM sensors 120 with an EM field, and the position of the rigid portion 105 may be confirmed based on input received from camera 110. Alternatively, an initial position of the rigid portion 105 of the surgical tool may be determined based on input received from camera 110, and the position of the rigid portion 105 may be confirmed based on an assessed location of the EM sensors 120.

In some examples, two EM sensors may be positioned within a surgical tool. In examples where the two EM sensors are positioned obliquely with respect to one another, a positional state of the surgical tool may be determined in six degrees of freedom. In some examples, EM sensors, such as EM sensors 120 of FIG. 1, may be positioned within surgical tools in different configurations. EM sensors may be formed of coils wrapped around a ferrous core. In examples, the ferrous core may comprise ferrites. In additional examples, the ferrous core may comprise soft ferrites. In further examples, the ferrous core may comprise hard ferrites. In some examples, the ferrous core may comprise a high permeability metal alloy. The diameter of each EM sensor may be 300 µm. In examples, the diameter of an EM sensor may be 250 µm, may be 200 µm, may be 150 µm, may be 100 µm, may be 50 µm, or may be less than 50 µm. In further examples, the diameter of an EM sensor may be 350 µm, may be 400 µm, may be 450 µm, may be 500 µm, may be 800 µm, 1 mm, 1.5 mm, or may be more than 1.5 mm. Additionally, in examples, the outer diameter of the EM sensor may be minimized. Two examples of configurations of EM sensors are provided in FIGS. 2A and 2B. In particular, FIGS. 2A and 2B illustrate configurations of two EM sensors within an endoscopic tip, in accordance with some embodiments.

Figure 2A:
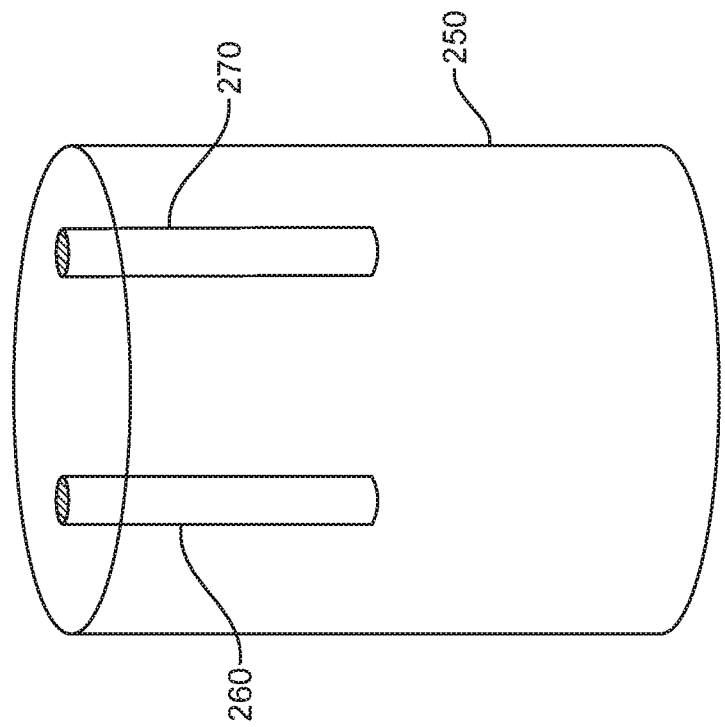
FIGS. 2A and 2B illustrate configurations of two EM sensors within an endoscopic tip, in accordance with some embodiments.

FIG. 2A illustrates an endoscopic tip 200 having EM sensors 210, 220 positioned obliquely with respect to one another. In some examples, the two sensors 210, 220 may be placed at a same distance from an end of the endoscope. In some examples, one of sensors 210, 220 may be placed closer to a tip of an endoscope and one of sensors 210, 220 may be placed further from a tip of an endoscope. Positioning EM sensors 210, 220 oblique to each other provides a benefit of assessing orientation of a surgical tool in addition to assessing a location of the surgical tool. In particular, interactions of the EM sensors 210, 220 with a generated EM field may be assessed to determine yaw, pitch, and roll of a portion of a surgical tool that contains EM sensors 210, 220. This determination is made based on the voltage that is produced by each EM sensor 210, 220 as each sensor passes through the EM field. In examples, the voltage is generated by the intersection of an electric field of the sensor with the magnetic flux lines in the EM field. The change in voltage may then be used to determine the spatial position of each sensor as the sensors move within a controlled volume, such as a controlled volume that contains the EM field. Additionally, when the EM sensors are positioned obliquely to one another, as seen in EM sensors 210, 220 of FIG. 2A, the difference in angled position may be assessed to determine an orientation of the surgical tool containing the EM sensors, such as endoscopic tip 200 that contains EM sensors 210, 220. In additional examples, the EM sensors may be positioned acutely to one another (not shown). When the EM sensors are positioned acutely to one another, the difference in angled positioned may also be assessed to determine an orientation of the surgical tool containing the EM sensors.

Figure 2B:
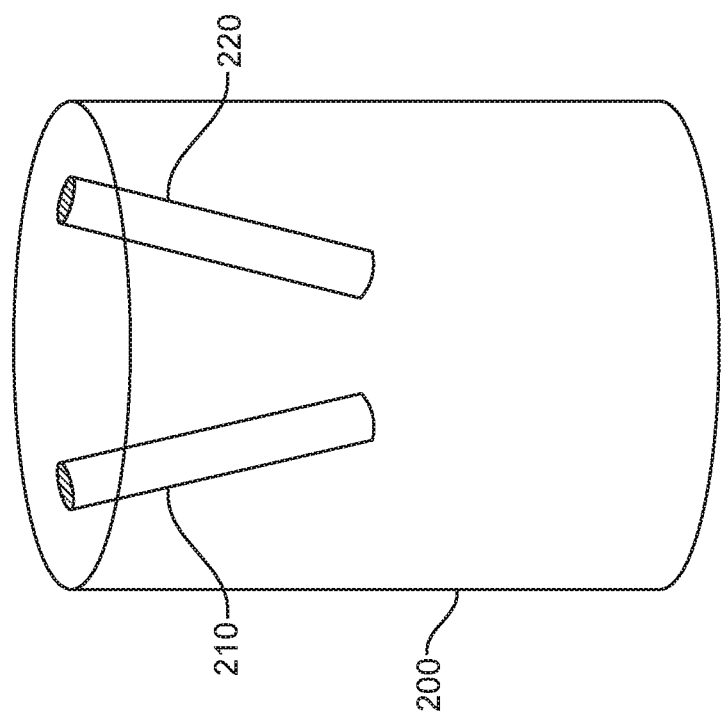

In contrast, FIG. 2B illustrates an endoscopic tip 250 having EM sensors 260, 270 positioned generally parallel to one another. Given that EM sensors 260, 270 have generally the same orientation, the sensors may be used to determine a location of the endoscopic tip 250 within a patient. In particular, the interaction of sensors 260, 270 with an EM field may be used to generate a voltage which may identify a location of the endoscopic tip 250 that includes sensors 260, 270 within three-dimensional special coordinates. However, since the sensors 260, 270 are not positioned at an oblique or acute angle with respect to each other, it may be more difficult to assess a particular orientation of the endoscopic tip 250. In particular, when sensors 260, 270 share a same general orientation, it may be more difficult to distinguish each of the sensors 260, 270 from the other. In examples where the sensitivity of the detection of the sensors 260, 270 is high enough, though, that the sensors 260, 270 may be distinguished from each other even as the sensors 260, 270 are generally parallel, the tracking of the individual sensors 260, 270 with respect to each other may be used to assess these additional three degrees of freedom. Even in this example, however, providing EM sensors at different orientations would provide a benefit of more easily distinguishing each of the EM sensors from one another, as discussed in FIG. 2A.

Although FIGS. 2A and 2B illustrate endoscopic tips 200, 250 having EM sensors 210, 220 and 260, 270, respectively, additional examples may be provided where an endoscopic tip has one EM sensor integrated therein. For example, an endoscopic tip may have one EM sensor integrated therein at a position similar to EM sensor 210 within endoscopic tip 200; similar to EM sensor 220 within endoscopic tip 200; similar to EM sensor 260 within endoscopic tip 250; or similar to EM sensor 270 within endoscopic tip 250. In additional examples, an EM sensor may be located near a central axis of an endoscopic tip. In particular, an EM sensor may partially overlap a central axis of the endoscopic tip. In further examples, an EM sensor may be located near the periphery of the endoscopic tip.

The one or more EM sensors may be tracked using an EM tracking surgical system, as discussed below in FIG. 3. In particular, an EM tracking surgical system may be provided in which field generator coils are provided so as to generate an EM field over at least a portion of a surgical bed. In examples, field generator coils may be incorporated within a surgical bed, and/or the field generator coils may be otherwise positioned relative to the surgical bed and/or to a patient on the surgical bed. As the one or more EM sensors of a surgical tool interact with the EM field, the location of the surgical tool may be determined. Additionally, movements of the surgical tool may be tracked based on the interactions with the EM field.

In additional examples, when two EM sensors are positioned within a surgical tool such that one of the two EM sensors has an extended core, the measured difference between the two EM sensors may be assessed to provide additional sensitivity with respect to the location of the surgical tool. Further, in examples when an extended core of an EM sensor is extended externally from the surgical tool, a force perception component may be utilized to determine a position of the surgical tool with respect to nearby tissue that is detected using the externally extended core of the EM sensor.

In additional examples, EM sensors may be placed along a surgical tool so as to determine a shape and location of the surgical tool within a patient. For example, a plurality of EM sensors may be placed along a surgical tool, such as a catheter. By setting EM sensors at predetermined distances along a surgical tool, the interactions of the EM sensors with a generated field may be assessed individually and collectively so as to determine characteristics about the position of the surgical tool with respect to the patient.

2. Tracking Surgical System Components

FIG. 3 illustrates a schematic of an EM tracking surgical system, in accordance with some embodiments. As shown in FIG. 3, EM tracking surgical system 300 may comprise a surgical bed 302 on a base 301, a plurality of field generator coils 303, an EM system controller 308, a switch module 310, a working volume 312, and a position sensor 316.

The surgical bed 302 may be configured to support a patient. A physician may perform a surgical procedure on the patient while the patient is placed on the surgical bed 302. In some embodiments, the surgical bed 302 may comprise multiple sections that are movable relative to one another. In those embodiments, the patient's body can be moved into different positions by moving different sections of the surgical bed 302 relative to one another. Alternatively, the surgical bed 302 may be formed monolithically as a single rigid structure.

Field generator coils 303 may be embedded or integrated along edge portions of the surgical bed 302. For example, as shown in FIG. 3, the plurality of field generator coils 303 may be embedded along a length of the surgical bed 302 in two rows. The rows may extend parallel to each other along the edge of the surgical bed 302. The placement of the field generator coils 303 along the edges of the surgical bed 302 can allow unobstructed use of fluoroscopy to image the patient's body during a surgical procedure. In additional embodiments, the field generator coils may be placed in other positions within, or around, the surgical bed 302 so as to generate a working volume 312 that may be used to track sensor 316. In some examples, the field generator coils may be incorporated within the surgical bed 302. In further examples, the field generator coils may be otherwise positioned relative to a patient and/or a surgical bed 302.

In examples, the shape of the working volume 312 may be determined based on the shape and strength of the EM field generated by the field generator coils 303 as activated by the EM system controller 308. In particular, the strength of the EM field that is generated may be controlled by EM system controller 308. In some examples, the working volume 312 may be defined by the volume that includes the presence of an EM field that is strong enough to generate a detectable voltage when it interacts with an EM sensor 316, such as EM sensors that may be disposed within surgical tools. In examples, an EM field may have the strength of 1 nanotesla (nT), 10 nT, 100 nT, 500 nT, 1 microtelsa (µT), 10 µT, 100 µT, 500 µT, 1 millitesla (mT), 10 mT, 100 mT, or more than 100 mT.

The field generator coils 303 may be fixed in place relative to one another. For example, the field generator coils may be spaced apart by a predetermined distance and/or at a predefined pitch along the edges of the surgical bed 302. In examples, the field generator coils may be nominally fixed relative to the surgical bed 302 in a global coordinate system. Any portion of the surgical bed 302 may serve as an origin of the global coordinate system. In some embodiments, a datum point that lies substantially above a center portion of the surgical bed 302 may serve as the origin of the global coordinate system. In those embodiments, the positions of the field generator coils may be defined relative to the datum point.

In some embodiments, when the surgical bed 302 comprises multiple sections that are movable relative to one another, the field generator coils 303 may not be fixed in position relative to one another. Instead, the field generator coils 303 may be located on one or more movable sections, and can move relative to one another when one or more sections of the surgical bed 302 move. In those embodiments, global tracking of a surgical tool can be facilitated by adding sensors to the surgical bed 302 that can detect changes in the configuration of the surgical bed 302.

As shown in FIG. 3, working volume 312 may be generated based on the placement of field generator coils 303. In particular, an EM system controller 308 may be configured to provide electrical current pulses to the field generator coils 303 to generate an EM field comprising the working volume 312. The EM system controller 308 can selectively activate or unactivate the EM field by controlling one or more switches in the switch module 310. In particular, electrical current pulses may be provided from the EM system controller 308 to the field generator coils 303 via one or more switches in the switch module 310.

The switches may include electronic switches such as power MOSFETs, solid state relays, power transistors, and/or insulated gate bipolar transistors (IGBTs). Different types of electronic switches may be provided for controlling current to the field generator coils 303. An electronic switch may utilize solid state electronics to control current flow. In some instances, an electronic switch may have no moving parts and/or may not utilize an electro-mechanical device (for example, but not limited to, traditional relays or switches with moving parts). In some instances, electrons or other charge carriers of the electronic switch may be confined to a solid state device. The electronic switch may optionally have a binary state (for example, but not limited to, switched-on or switched-off). The electronic switches may be used to control current flow to the field generator coils. The operation of switches to selectively activate the field generator coils 303 is described with reference to FIG. 4, below.

In some embodiments, the EM system controller 308 may be located on the surgical bed 302, for example on a base 301 configured to support the surgical bed 302. In some embodiments, the EM system controller 308 may be located remotely from the surgical bed 302. For example, the EM system controller 308 may be disposed in a remote server that is in communication with the field generator coils 303 and the switch module 310. The EM system controller 308 may be software and/or hardware components included with the server. The server can have one or more processors and at least one memory for storing program instructions. The processor(s) can be a single or multiple microprocessors, field programmable gate arrays (FPGAs), or digital signal processors (DSPs) capable of executing particular sets of instructions. Computer-readable instructions can be stored on a tangible non-transitory computer-readable medium, such as a flexible disk, a hard disk, a CD-ROM (compact disk-read only memory), and MO (magneto-optical), a DVD-ROM (digital versatile disk-read only memory), a DVD RAM (digital versatile disk-random access memory), or a semiconductor memory. Alternatively, the program instructions can be implemented in hardware components or combinations of hardware and software such as, for example, ASICs, special purpose computers, or general purpose computers.

The EM system controller 308 may also be provided at any other type of external device (for example, but not limited to, a remote controller for controlling the surgical bed 302 and/or a surgical tool, any movable object or non-movable object, etc.). In some instances, the EM system controller 308 may be distributed on a cloud computing infrastructure. The EM system controller 108 may reside in different locations where the EM system controller 303 is capable of controlling the switch module 310 and selectively activating the field generator coils 303 based on the spatial information of the position sensor 316. For instance, EM system controller 108 may activate an FG coil when a position sensor comes within a threshold distance of the FG coil. Additionally, EM system controller 308 may de-activate an FG coil when a position sensor moves beyond a threshold distance from the FG coil.

The position sensor 316 may be disposed in or on a portion of a surgical tool. For example, in some embodiments, the position sensor 316 may be disposed at a distal end of the surgical tool. Examples of surgical tools may include endoscopes, catheters, ureteroscopes, forceps, different kinds of scopes, or other similar devices or surgical accessories.

A position sensor, such as position sensor 316, may be configured to generate an electrical signal (for example, but not limited to, voltage or current signal) in response to EM fields generated by the field generator coils 303. Position sensor 316 may be an EM sensor. As position sensor 316 moves within a control volume 312, the interaction of the position sensor 316 with the EM field within the control volume 312 may cause electrical signals to be generated. The electrical signals may vary as the position sensor 316 moves between different locations within a control volume 312. Additionally, electrical signals may vary as the position sensor 316 moves between different control volumes. The EM system controller 308 may be configured to receive electrical signals from the position sensor 316. Additionally, the EM system controller 308 may analyze the signals to compute a local position of the sensor 316. The local position of the sensor 316 may be computed relative to a local coordinate system. The local coordinate system may be defined at active field generator coils 303 corresponding to the control volume 312 in which the position sensor 316 is located.

The EM system controller 308 may be further configured to compute a global position of the sensor 316 relative to a global coordinate system. The global coordinate system may be defined at the surgical bed 302 (for example, but not limited to, above a center portion of the surgical bed 302). The global position of the sensor 316 may be computed based on: (1) the local position of the sensor 316 within the control volume 312 above active field generator coils 303, and (2) the position of the active field generator coils 303 relative to the surgical bed 302. The global position of the sensor 316 may be used to determine a position of a surgical tool relative to a patient on the surgical bed 302. Additionally, the EM system controller 308 may be configured to control the switch module 310 based on one or more inputs. The control of the switch module 310, and the selective activation of one or more subsets of field generator coils 303, may be manual and/or automatic.

In some embodiments, the EM system controller 308 may control the switch module 310 based on a user input corresponding to a selection of a region (or working volume 312) of the surgical bed 302 where tracking of a surgical tool is desired. For example, a physician may plan to perform a surgical procedure on a patient in a region within the working volume 312. Accordingly, the physician or the physician's assistant may provide an input to the EM system controller 308 to activate the field generator coils 303, so that movement of the surgical tool can be tracked within the first control volume via the position sensor 316.

In some embodiments, a local position of the sensor 316 may be determined based on distances between the sensor 316 and a plurality of reference points in different local coordinate systems. The different local coordinate systems may within and/or outside control volume 312. The EM system controller 308 may be configured to determine a minimum distance from those distances, and activate field generator coils 303 corresponding to the control volume 112 based on the minimum distance. Additionally, during a surgical procedure, the EM system controller 308 may be configured to track the position and/or movement of the sensor 316 within a control volume 312 corresponding to active field generator coils 303.

3. Switching Circuit

Figure 4:
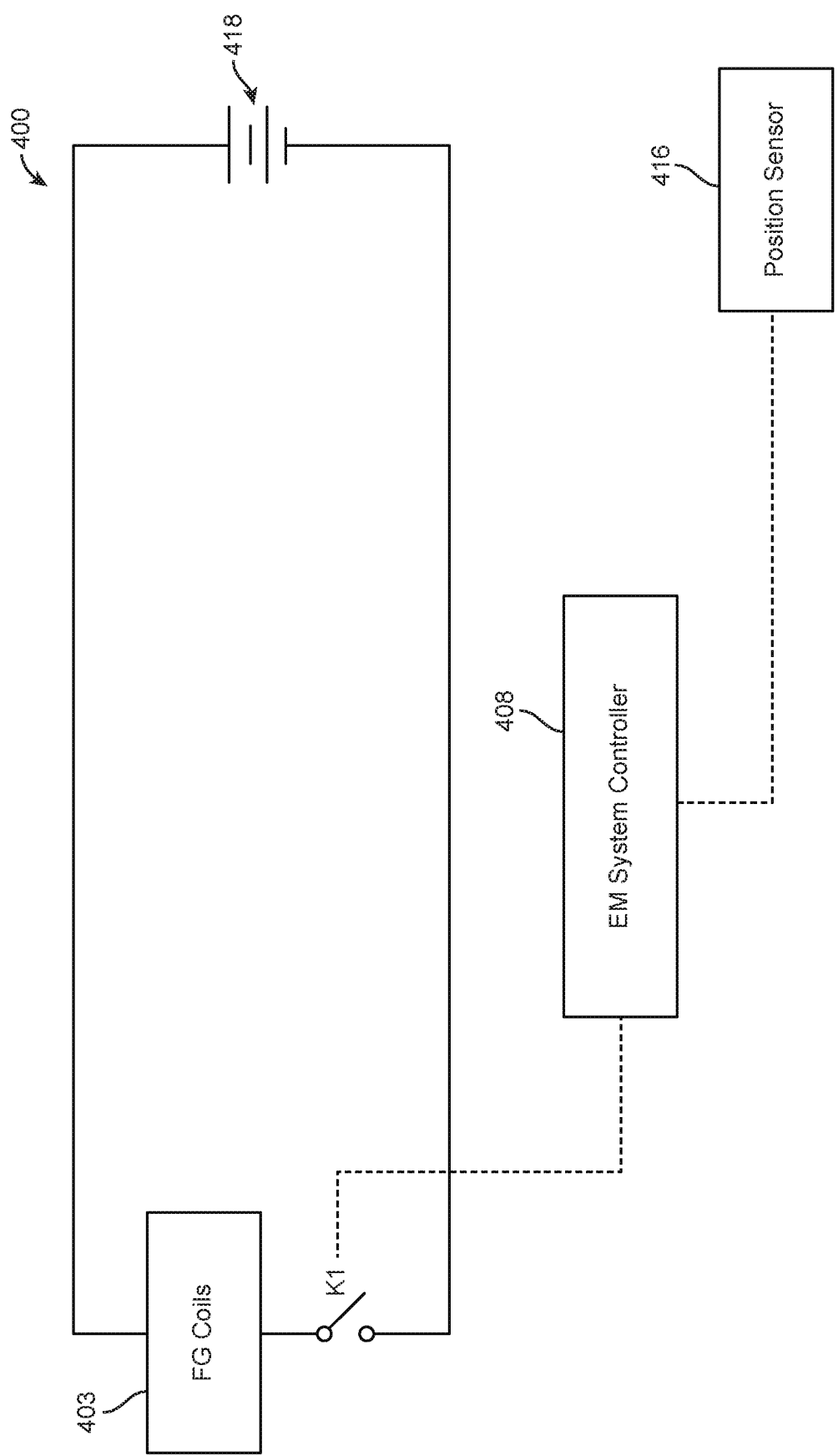
FIG. 4 illustrates a schematic circuit diagram of an EM tracking surgical system, in accordance with some embodiments.

FIG. 4 illustrates a schematic circuit diagram of an EM tracking surgical system, in accordance with some embodiments. As shown in FIG. 4, an EM tracking surgical system 400 may comprise field generator coils 403 electrically connected to a power supply 418. An EM system controller 408 may be in operable communication with a switch K1 and a position sensor 416. Switch K1 may be located in a switch module (for example, but not limited to, switch module 310 of FIG. 3). The EM system controller 408 may be configured to selectively activate field generator coils 403 based on a position and/or movement of the position sensor 416 within and/or outside a control volume (for example, but not limited to, control volumes 312 of FIG. 3).

In examples, an EM system controller 408 may activate field generator coils when a position sensor 416 within a surgical tool indicates that the surgical tool is nearing a working volume that is associated with a patient. For example, an EM system controller 408 may activate field generator coils when a position sensor 416 within a surgical tool indicates that the surgical tool is within a threshold distance of a working volume that is associated with the patient. In examples, the threshold distance may be less than 1 mm, 1 mm, 2 mm, 3 mm, 4 mm, 5 mm, 6 mm, 8 mm, 10 mm, or more than 10 mm. In additional examples, an EM system controller 408 may de-activate field generator coils 403 when a position sensor 416 within a surgical tool indicates that the surgical tool has left a working area that is associated with a patient. For example, an EM system controller 408 may de-activate field generator coils when a position sensor 416 within a surgical tool indicates that the surgical tool is beyond a threshold distance of a working volume that is associated with the patient. In examples, the threshold distance may be less than 1 mm, 1 mm, 2 mm, 3 mm, 4 mm, 5 mm, 6 mm, 8 mm, 10 mm, or more than 10 mm. The EM system controller 408 may also activate field generator coils 403 in response to receiving a request to initiate the field generator coils 403. In additional examples, the EM system controller 408 may de-activate the field generator coils 403 when a predetermined amount of time has passed without sensing movement of the position sensor 416.

4. Examples of Surgical Tool Components

Figure 5:
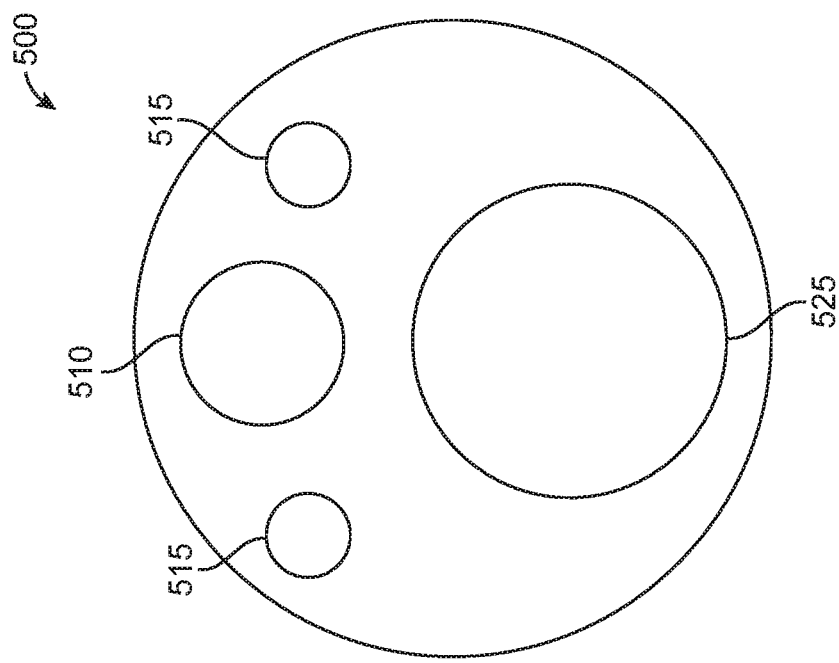
FIG. 5 illustrates a front view of an endoscopic tip having EM sensors within, in accordance with some embodiments.

In examples, EM sensors may be completely internalized within a surgical component. As such, an external view of a surgical component may not directly indicate the presence of EM sensors. In accordance with this example, FIG. 5 illustrates a front view 500 of an endoscopic tip having EM sensors (not shown) fully integrated within. Having EM sensors fully integrated within provides a benefit of encapsulating the sensor materials so as to prevent exposure of the sensor materials to the patient, as well as to prevent exposure of potential corrosive materials to the sensor materials. As seen in FIG. 5, an external view of endoscopic tip may provide a camera 510, illumination components 515, and a working channel 525.

While the placement of EM sensors may be completely internalized within a surgical tool, the placement of other components of the endoscopic tip as seen in FIG. 5 may be affected by internalized EM sensors within the endoscopic tip. In particular, other components within a surgical tool, such as an endoscopic tip, may be arranged based on placement of the one or more sensors. For example, illumination sources 515 may be placed closer to a proximate edge of a face of an endoscopic tip so as to allow an area for one or more EM sensors to reside internally within the endoscopic tip. Additionally, while two illumination sources are illustrated in FIG. 5, other examples may provide a single illumination source. In additional examples, more than two illumination sources may be provided. For example, three, four, five, six, seven, eight, or more than eight illumination sources may be provided. In these examples, the placement of the illumination sources may be configured so as to allow for the placement of at least one EM sensor within a portion of a surgical tool, such as within an endoscopic tip of the surgical tool.

Figure 6:
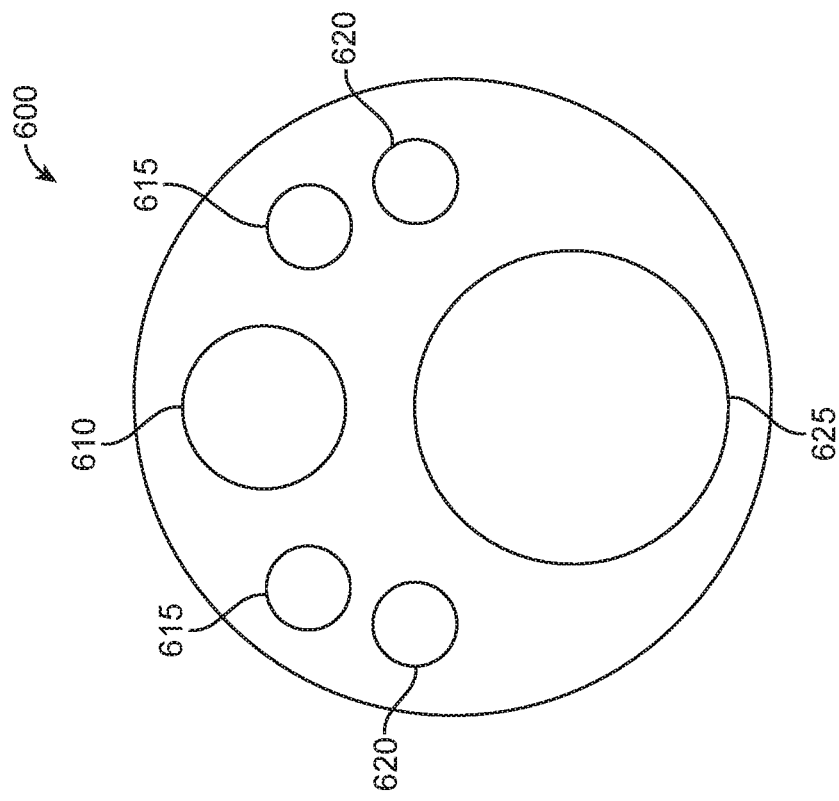
FIG. 6 illustrates a view of an internal cross-section of an endoscopic tip having EM sensors within, in accordance with some embodiments.

An example of a cross-section of an endoscopic tip having internalized EM sensors is provided in FIG. 6. In particular, FIG. 6 illustrates a view 600 of an internal cross-section of an endoscopic tip having EM sensors 620 within, in accordance with some embodiments. As seen in FIG. 6, EM sensors 620 are positioned relative to a camera 610, illumination sources 615, and a working channel 625. In particular, EM sensors 620 are positioned between illumination sources 615 and the working channel 625. While two EM sensors 620 are illustrated in FIG. 6, in other examples a single EM sensor may be provided. In additional examples, more than two EM sensors may be provided. For example, three, four, five, six, seven, eight, or more than eight EM sensors may be provided. Additionally, each EM sensor does not need to be within a same area of the surgical tool. Although the two EM sensors as shown in FIG. 6 are both within a tip of an endoscope, additional examples may provide that EM sensors are provided in staggered placement along a length of a surgical tool and/or along a length of a tip of an endoscope. Additionally, staggered positioning of EM sensors may provide for an effective lengthening of a sensor area that induces voltage change when exposed to an EM field. This, in turn, may make a a location and/or orientation of a surgical tool more readily identifiable.

Figure 7:
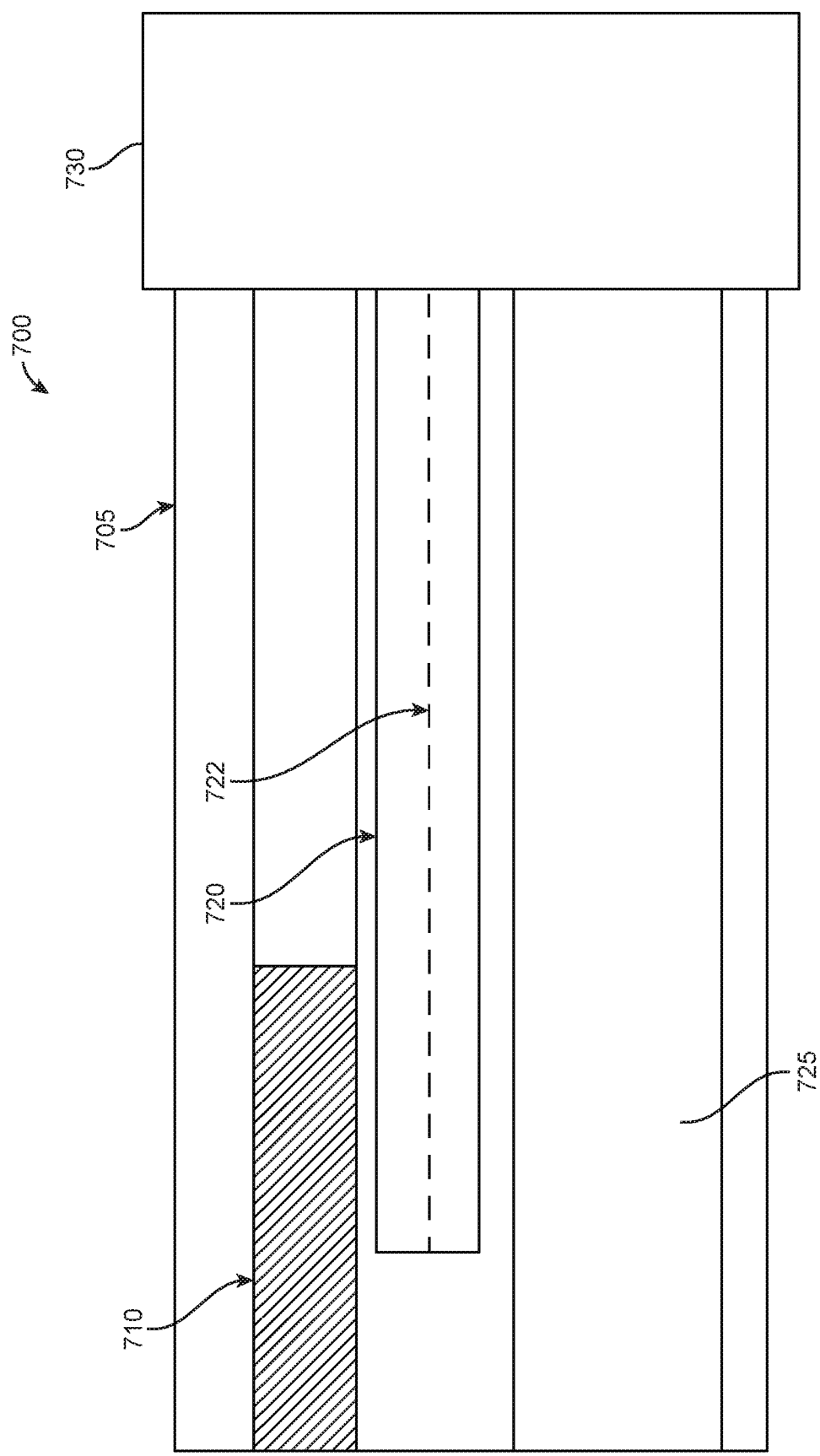
FIG. 7 illustrates a side view of a cross-section of an endoscope with EM sensors within, in accordance with some embodiments.

FIG. 7 illustrates a side view 700 of a cross-section of a portion of an endoscope with EM sensors within, in accordance with some embodiments. In particular, FIG. 7 illustrates a rigid portion 705, a camera 710, a first EM sensor 720 having a core 722, a working channel 725, and a flexible portion 730. Rigid portion 705 may be attached to flexible portion 730. As seen in FIG. 7, a core 722 of a first EM sensor 720 may stay within the rigid portion 705 of the endoscope. In some examples, the length of the core 722 of the first EM sensor may match the length of the coil that surrounds the core 722 of the EM sensor. In additional examples, coil that surrounds the core 722 of the EM sensor may have a short length. In some examples, coil of EM sensor 720 may surround the core 722 of the EM sensor continuously. In further examples, coil of the EM sensor 720 may surround the core of the EM sensor discontinuously.

While FIG. 7 illustrates a first EM sensor 720, the rigid portion 705 may also comprise a second EM sensor (not shown). In examples, a length of a second EM sensor may match the length of the first EM sensor 720. In other examples, a length of a second EM sensor may be greater than the length of the first EM sensor. In further examples, a length of a second EM sensor may be shorter than the length of the first EM sensor.

In some examples having a first and a second EM sensor within a surgical tool, a core of a first EM sensor may be extended so as to increase sensitivity of voltage measurement. In particular, when a core of a first EM sensor is extended while the core of the second EM sensor remains constant, a voltage that is measured between the first and second EM sensors may be assessed to determine a magnitude and a direction of a generated magnetic field. This information may, in turn, be used to determine information associated with a change of position of the surgical tool having the first and second EM sensors integrated therein. Additionally, the determined magnitude and direction of a generated magnetic field may be used to determine a change in orientation of the surgical tool having the first and second EM sensors integrated therein.

Figure 8:
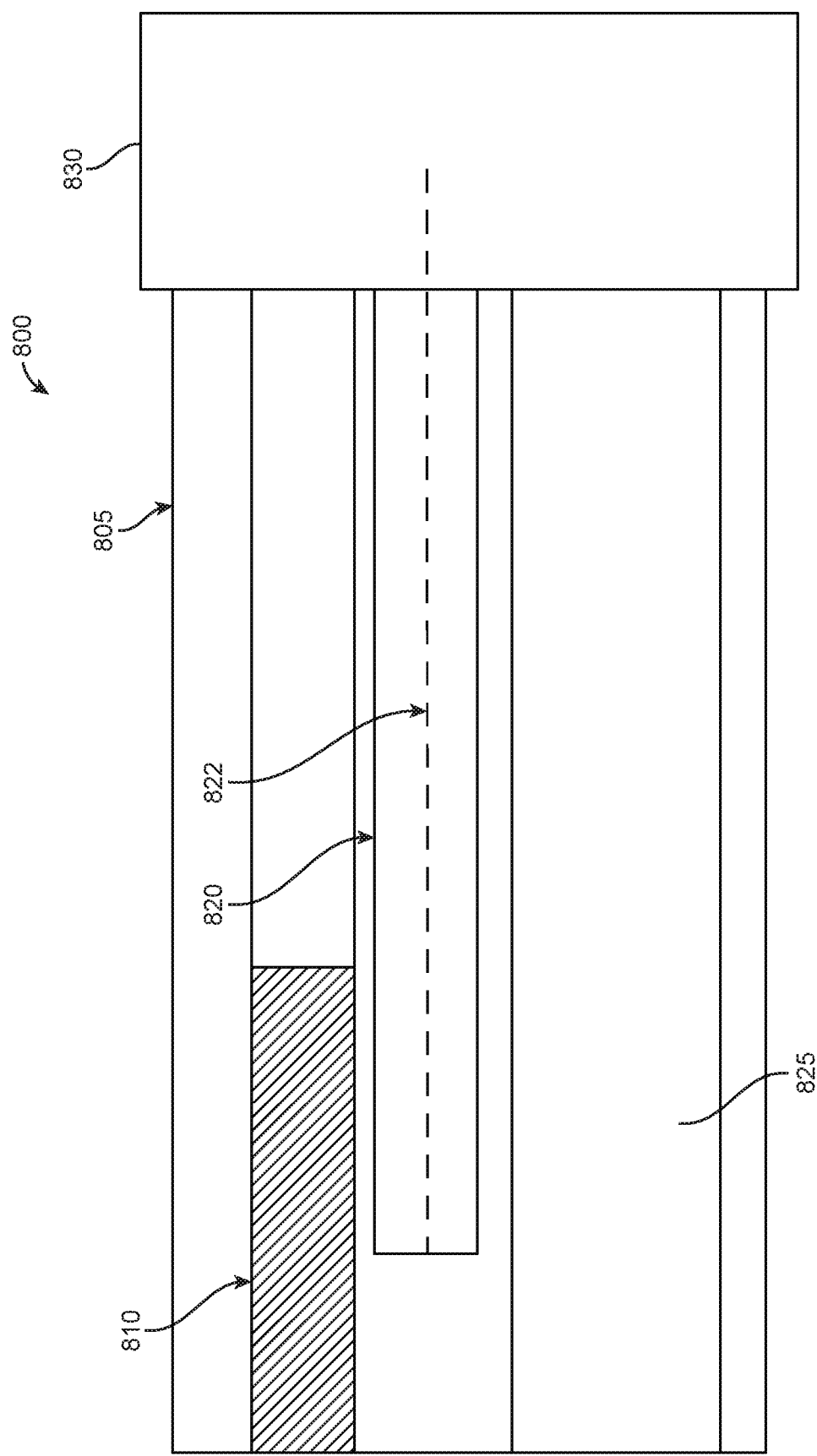
FIG. 8 illustrates a side view of a cross-section of an endoscope with EM sensors having an internally extending core, in accordance with some embodiments.

In examples, the first EM sensor 820 of the first and second EM sensors may have a core that is extended internally. In particular, FIG. 8 illustrates a side view 800 of a cross-section of an endoscope portion with an EM sensor 820 having an internally extending core 822, in accordance with some embodiments. FIG. 8 provides a first EM sensor 820 disposed between a camera 810 and a working channel 825 within an endoscope. As seen in FIG. 8, the internally extending core 822 extends from a rigid portion 805 of the endoscope to a flexible portion 830. As discussed above, extending a core of a first EM sensor 820 may increase the sensitivity when assessing a change in voltage induced by the first EM sensor 820 and the second EM sensor (not shown) interacting with an EM field generated by field generator coils that are activated by an EM controlling system.

In examples, the use of an extended core, such as extended core 822 of first EM sensor 820, can boost the sensitivity of voltage measurement induced by the interaction of the first EM sensor 820 and second EM sensor (not shown) with a generated EM field. In some examples, an EM sensor with an extended core may have increased sensitivity relative to an EM sensor without an extended core based on an aspect ratio of the EM sensor. In particular, by lengthening an EM sensor, sensitivity of the EM sensor may be improved. Similarly, minimizing a length of a sensor strip while maintaining a length of the core of an EM sensor may also increase an aspect ratio of the EM sensor, thereby also increasing sensitivity of the sensor. In additional examples, sensitivity of an EM sensor may be increased based on a material composition of the EM sensor. In further examples, sensitivity of an EM sensor may be affected by shape permeability. Shape permeability may be influenced by sensor orientation, size, and dimensions in addition to aspect ratio and core material as previously discussed.

Figure 9:
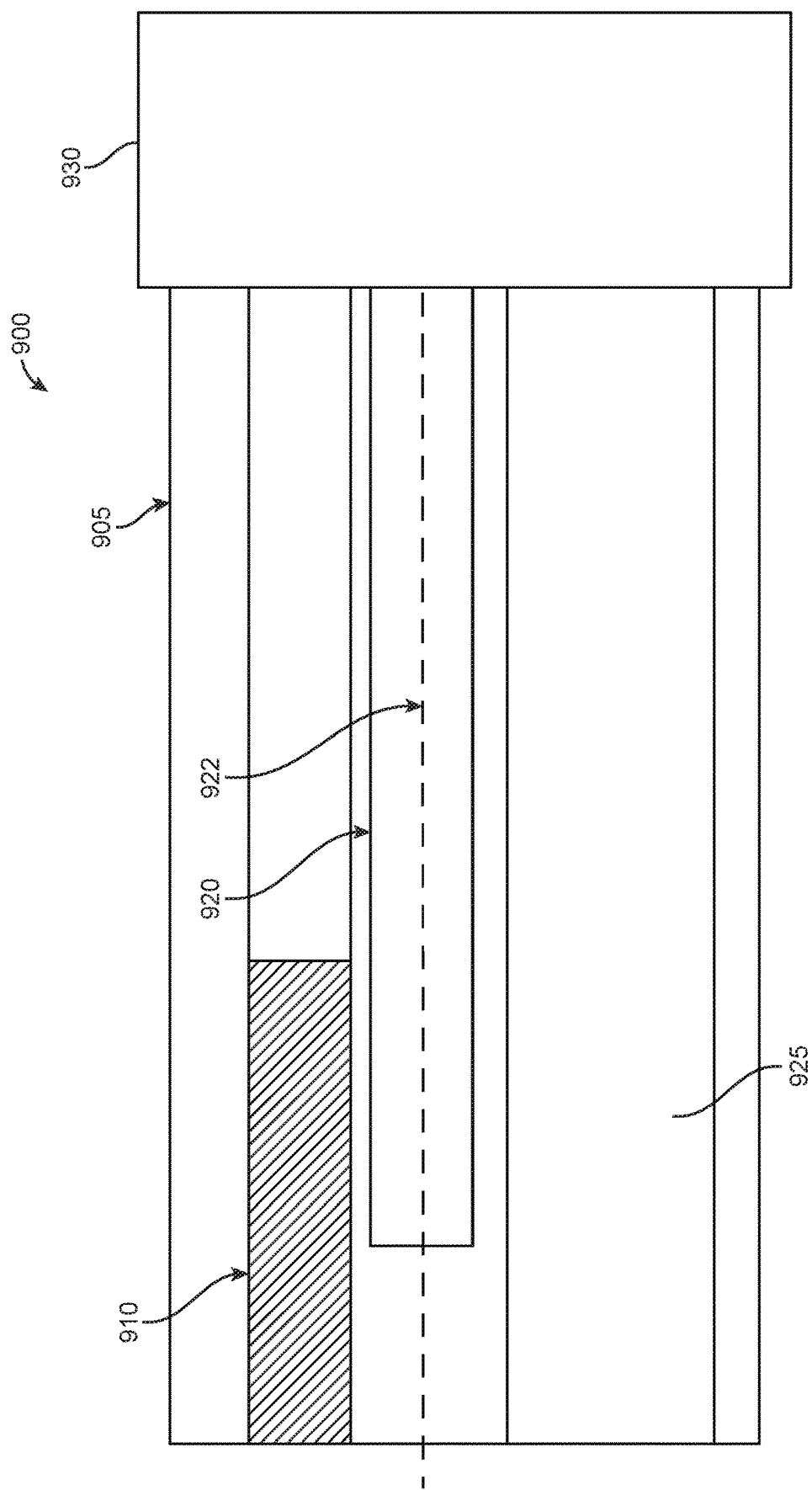
FIG. 9 illustrates a side view of a cross-section of an endoscope with EM sensors having an externally extending core, in accordance with some embodiments.

In other examples, the first EM sensor 920 of the first and second EM sensors may have a core that is extended externally. In particular, FIG. 9 illustrates a side view 900 of a cross-section of an endoscope portion with an EM sensor 920 having an externally extending core 922, in accordance with some embodiments. In some examples, a diameter of core 922 may be less than 1 mm, 1 mm, 2 mm, 3 mm, 4 mm, 5 mm, or more than 5 mm. FIG. 9 provides a first EM sensor 920 disposed between a camera 910 and a working channel 925 within an endoscope. As seen in FIG. 9, the externally extending core 922 extends from a rigid portion 905 of the endoscope to an external portion of the endoscope. As such, externally extending core 922 may contact tissue and other materials that may be found at a surgical location within a patient. In examples, the externally extending core 922 may be used to measure properties of materials, such as tissue, at a surgical site through the application of mechanical force and/or palpitations. In particular, the externally extending core 922 may be used to apply force or palpitations and/or may be used to measure the response of materials to the application of force or palpitations. As discussed above, extending a core of a first EM sensor 920 may increase the sensitivity when assessing a change in voltage induced by the first EM sensor 920 and the second EM sensor (not shown) interacting with an EM field generated by field generator coils that are activated by an EM controlling system.

In addition to benefits that may be provided from extending a core 922 of first EM sensor 920 based on the increased sensitivity of the EM sensor, an externally extended core 922 may also be used to obtain information based on applying a force to materials at a surgical site. In some examples, a force perception structure may be attached to a free end of an extended core. In some examples, the force perception structure may be ball-shaped so as to maximize surface area for contact as well as to minimize negative invasive effects when the force perception structure encounters materials, such as tissue, at a surgical site. In some examples, the force perception structure may be shaped as a pyramid, cylinder, cube, or a flat sheet, in addition to other examples. When the force perception structure comes into contact with material, the force perception structure may generate an output in response to the contact interaction. In additional examples, force applied to an extended core may be assessed based upon a degree of deflection when the extended core is pressed against tissue. In this example, the non-extended core of a second EM sensor may be used as reference point for differential measurement between the first EM sensor having an externally extended core and the second EM sensor that does not have an externally extended core. In additional examples, both the first and second EM sensors may have cores that are extended relative to a length of a coiled material provided around the core of the EM sensor. In these examples, however, the length and/or direction of core extension between the first and second EM sensor may differ so as to provide a greater differential between voltage measurements between the two sensors.

Figure 10:
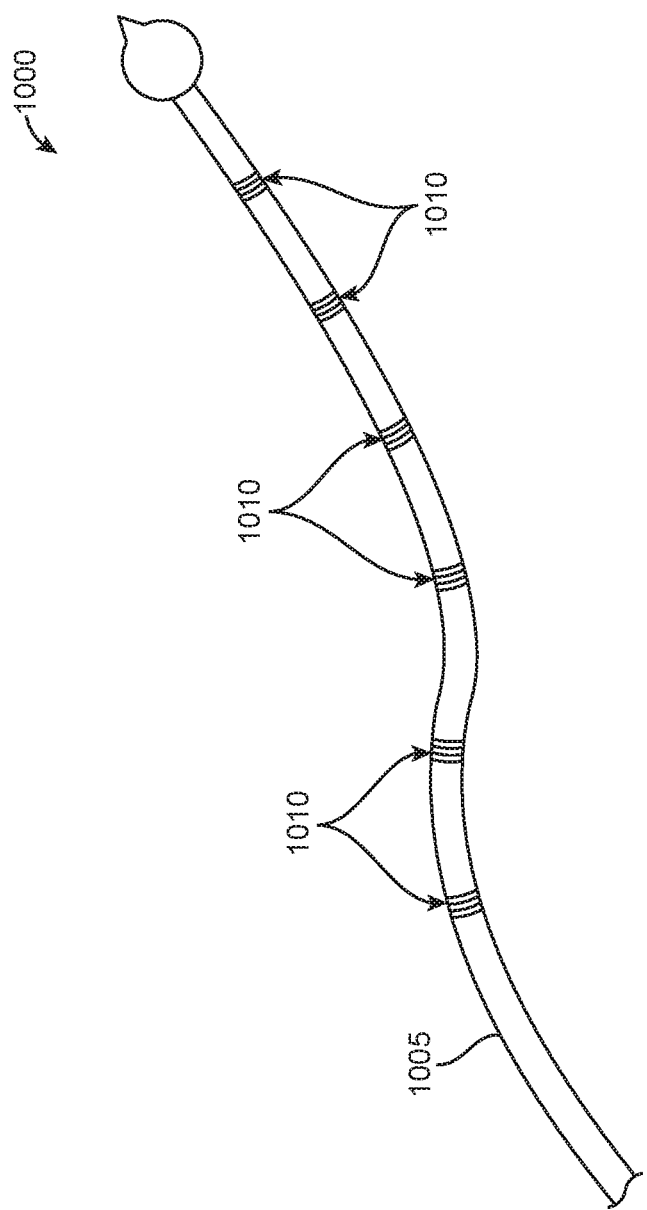
FIG. 10 illustrates a catheter having external EM sensors, in accordance with some embodiments.

While some examples of surgical tools may have EM sensors integrated within the surgical tool, other examples of surgical tools may have EM sensors integrated externally. In some examples, externally integrated EM sensors may be attached to the surgical tool. In particular, FIG. 10 illustrates a view 1000 of a catheter 1005 having external EM sensors 1010, in accordance with some embodiments. As seen in FIG. 10, the plurality of EM sensors 1010 are located at different locations along the length of the catheter 1005. Each of the EM sensors 1010 may generate a change in voltage when exposed to an electromagnetic field. By detecting this change in voltage, the location of the catheter may be determined. Additionally, as there may potentially be a number of location inputs, the change of voltage that is generated by the plurality of EM sensors 1010 may be used to determine a shape of the catheter 1005. Further, as the catheter moves within a patient, the change of shape of the catheter may also be determined based on the detected change of voltage that is measured.

In an example, a minimal interval distance may be provided between each EM sensor 1010 and a subsequent EM sensor. By providing a minimal interval distance, interference between EM sensors may be minimized. In some examples, the interval distance between two adjacent EM sensors may be in the range of 5-10 cm. In some examples, the interval distance may be less than 2 cm, 2 cm, 3 cm, 4 cm, 5 cm, 6 cm, 7 cm, 8 cm, 9 cm, 10 cm, 11 cm, 12 cm, 13 cm, 14 cm, 15 cm, 20 cm, or more than 20 cm. Additionally, the distance between each EM sensor may differ, such as within a particular distance. For example, EM sensors along a catheter may be between 5 cm and 10 cm apart. In some examples, the EM sensors along a catheter may be 5 cm apart. In some examples, the EM sensors along a catheter may be 10 cm apart. In some examples, the EM sensors along a catheter may be at least 5 cm apart. The spacing between EM sensors may be continuous, may be based on a pattern, and/or may be consistent within a threshold range of distances.

In additional examples, each EM sensor placed along a surgical tool may have a length that extends along the length of the shaft of the surgical tool that is between 2-4 mm. In some examples, the EM sensor may have a length along the shaft of the surgical tool of less than 1 mm, 1 mm, 2 mm, 3 mm, 4 mm, 5 mm, 6 mm, 7 mm, 8 mm, 9 mm, 10 mm, 20 mm, 30 mm, 40 mm, 50 mm, 60 mm, 70 mm, 80 mm, 90 mm, 1 cm, or more than 1 cm. Additionally, in examples, each EM sensor may comprise a core with coils wound around. The core may be a ferrous core. In examples, the core may be a type of ferrite.

7. EM Tracking Surgical Systems Having Reconfigurable Bed Portions

Figure 11:
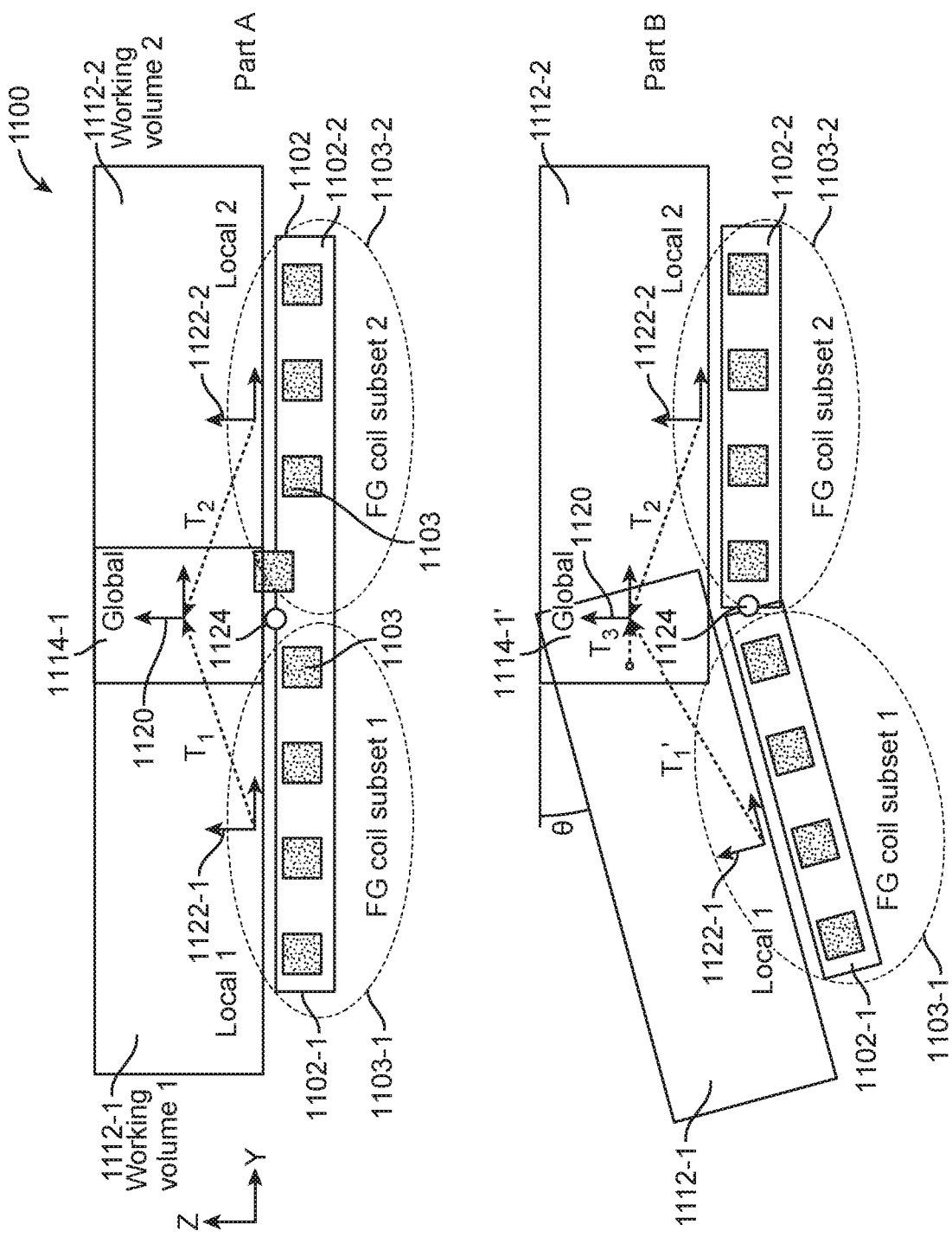
FIG. 11 illustrates schematic views of an EM tracking surgical system having reconfigurable bed portions, in accordance with some embodiments.

FIG. 11 illustrates schematic views of an EM tracking surgical system having reconfigurable bed portions, in accordance with some embodiments. Part A of FIG. 11 illustrates a side view of a portion of an EM tracking surgical system 1100 when a surgical bed is in a first position. Part B of FIG. 11 illustrates the side view of the system 1100 when the surgical bed is in a second position.

As shown in FIG. 11, a surgical bed 1102 may comprise reconfigurable bed portions that can move relative to each other. For example, the surgical bed 1102 may comprise a first bed portion 1102-1 and a second bed portion 1102-2 connected at a hinge 1124 that allows the bed portions to move (for example, but not limited to, rotate and/or slide) relative to each other. A first subset of field generator coils 1103-1 may be embedded along a length of the first bed portion 1102-1. A second subset of field generator coils 1103-2 may be embedded along a length of the second bed portion 1102-2. Accordingly, the first and second subsets of field generator coils 1103 may be embedded along a length portion of the surgical bed 1102.

A first working volume 1112-1 may be defined above the first subset of field generator coils 1103-1, and a second working volume 1112-2 may be defined above the second subset of field generator coils 1103-2. In some embodiments, the dimensions and/or size of the first and second working volumes 1112-1 and 1112-2 may be the same. Alternatively, the dimensions and/or size of the first and second working volumes 1112-1 and 1112-2 may be different.

As shown in FIG. 11, the first and second working volumes may overlap so as to form a first overlapping working volume 1114-1 disposed at a boundary between the first and second subsets of field generator coils 1103-1 and 1103-2. The first and second working volumes 1112-1 and 1112-2 may be configured to overlap by various amounts. For example, the first and second working volumes 1112-1 and 1112-2 may be configured to overlap by 1%, 2%, 5%, 10%, 15%, 20%, 25%, 30%, or more than 30%. The first and second working volumes 1112-1 and 1112-2 may be configured to overlap such that one or more position sensors, such as position sensors 1116 discussed above, can be accurately tracked and controlled near the boundaries of the control volumes 1112, and as the position sensor(s) 1116 moves between adjacent working volumes 1112.

As shown in FIG. 11, a global coordinate system 1120 may be defined above a center portion of the surgical bed 1102. For example, the global coordinate system 1120 may be defined above a boundary line between the first bed portion 1102-1 and the second bed portion 1102-2. An origin of the global coordinate system 1120 may lie above the center portion of the surgical bed 1102 along the Z-direction. The origin of the global coordinate system 1120 may also lie at a predetermined location above the hinge 1124 when the surgical bed is in the position shown in part A of FIG. 11. The origin of the global coordinate system 1120 may serve as a datum point from which the positions of a patient's body, the field generator coils 1103, and the working volume 1112 may be defined.

A first local coordinate system 1122-1 may be defined above a center portion of the first bed portion 1102-1. Likewise, a second local coordinate system 1122-2 may be defined above a center portion of the second bed portion 1102-2. The first local coordinate system 1122-1 may or may not have an origin that lies at a center portion of the first working volume 1112-1. Similarly, the second local coordinate system 1122-2 may or may not have an origin that lies at a center portion of the second working volume 1112-2. For example, as shown in part A of FIG. 11, the origin of the first local coordinate system 1122-1 may lie below the center portion of the first working volume 1112-1, and in close proximity to the first bed portion 1102-1. Likewise, the origin of the second local coordinate system 1122-2 may lie below the center portion of the second working volume 1112-2, and in close proximity to the second bed portion 1102-2.

Vectors may be defined between the global coordinate system 1120 and the local coordinate systems 1122-1 and 1122-2. For example, a vector T1 may be defined from the origin of the first local coordinate system 1122-1 to the origin of the global coordinate system 1120. A vector T2 may be defined from the origin of the second local coordinate system 1122-2 to the origin of the global coordinate system 1120. In some embodiments, another vector (not shown) may be defined from the origin of the first local coordinate system 1122-1 to the origin of the second local coordinate system 1122-2. The vectors T1 and T2 may be used to define the spatial relationship between the first working volume 1112-1 and the second working volume 1112-2. In particular, the vectors T1 and T2 may be used to define the spatial relationship between the first and second working volumes 1112-1 and 1112-2 relative to the datum point (for example, but not limited to, origin of the global coordinate system 1120) as the first and second bed portions 1102-1 and 1102-2 move relative to each other.

As shown in part A of FIG. 11, the first bed portion 1102-1 and the second bed portion 1102-2 may initially lie on a same horizontal plane extending along the Y-axis direction. The first and second bed portions 1102-1 and 1102-2 may be configured to move relative to each other. For example, as shown in part B of FIG. 11, the first bed portion 1102-1 may rotate by an angle θ in a clockwise direction about an X-axis extending through the hinge 1124. The first bed portion 1102-1 may be rotated, for example, to lower or raise a portion of a patient's body that is supported by the first bed portion 1102-1. Since the first control volume 1112-1 is defined by the EM field generated by the first subset of field generator coils 1103, the first control volume 1112-1 may also rotate by the angle θ in a clockwise direction about the X-axis. As shown in part B of FIG. 11, it may be observed that the origin of the first local coordinates system 1122-1 has shifted to a new location. Accordingly, a new vector T1' may be defined from the shifted origin of the first local coordinates system 1122-1 to the origin of the global coordinates system 1120, whereby the vector T1' is different from the vector T1. Since the second bed portion 1102-2 is not rotated relative to the global coordinates system 1120, the origin of the second local coordinates system 1122-2 remains unchanged, and therefore the vector T2 remains the same. The vectors T1' and T2 may be used to define the spatial relationship between the first and second working volumes 1112-1 and 1112-2 relative to the datum point (for example, but not limited to, origin of the global coordinate system 1120) after the first bed portion 1102-1 has moved relative to the second bed portion 1102-2.

Although part B of FIG. 11 illustrates movement of the first bed portion 1102-1 relative to the second bed portion 1102-2, the movement between the bed portions is not limited thereto. For example, in some embodiments, the second bed portion 1102-2 may move relative to the first bed portion 1102-1. Optionally, the first and second bed portions 1102-1 and 1102-2 may simultaneously move relative to each other such that the origins of the first and second local coordinate systems shift to different locations. The relative movement between the bed portions 1102-1 and 1102-2 may comprise a rotational motion, a translational motion, and/or a combination of rotational and translational motion, about one or more axes. Accordingly, relative movement of the bed portions 1102-1 and 1102-2 in one or more degrees of freedom (for example, but not limited to, six degrees of freedom) may be contemplated.

In some embodiments, a position, shape, and/or size of the overlapping working volume 1114 between adjacent working volumes may change when the bed portions move relative to each other. For example, as shown in part A of FIG. 11, a center (or centroid) of the first overlapping working volume 1114-1 may be located at the origin of the global coordinates system 1120. The first overlapping working volume 1114-1 may have a regular shape (for example, but not limited to, defined by a length U1, width W, and height H).

When the first bed portion 1102-1 rotates relative to the second bed portion 1102-2, the position, shape, and/or size of the first overlapping working volume 1114-1 may change. For example, as shown in part B of FIG. 11, the first overlapping working volume 1114-1 may transform to overlapping working volume 1114-1' having an irregular shape (for example, but not limited to, having a trapezoidal-like profile as viewed from a side of the overlapping working volume 1114-1'). The origin of the global coordinates system 1120 remains unchanged by the relative rotation of the bed portions. Unlike part A of FIG. 11, the center (or centroid) of the overlapping working volume 1114-1' is not located at the origin of the global coordinates system 1120 after the rotation. Instead, the center (or centroid) of the overlapping working volume 1114-1' may be offset from the origin of the global coordinates system 1120 by a vector T3 after the rotation.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including," when used in this specification, specify the presence of stated features, regions, integers, steps, operations, elements and/or components, but do not preclude the presence or addition of one or more other features, regions, integers, steps, operations, elements, components and/or groups thereof Furthermore, relative terms, such as "lower" or "bottom" and "upper" or "top" may be used herein to describe one element's relationship to other elements as illustrated in the figures. It will be understood that relative terms are intended to encompass different orientations of the elements in addition to the orientation depicted in the figures. For example, if the element in one of the figures is turned over, elements described as being on the "lower" side of other elements would then be oriented on the "upper" side of the other elements. The exemplary term "lower" can, therefore, encompass both an orientation of "lower" and "upper," depending upon the particular orientation of the figure. Similarly, if the element in one of the figures were turned over, elements described as "below" or "beneath" other elements would then be oriented "above" the other elements. The exemplary terms "below" or "beneath" can, therefore, encompass both an orientation of above and below.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Numerous different combinations of embodiments described herein are possible, and such combinations are considered part of the present disclosure. In addition, all features discussed in connection with any one embodiment herein can be readily adapted for use in other embodiments herein. It is intended that the following claims define the scope of the invention and that methods and structures within the scope of these claims and their equivalents be covered thereby.

What is claimed is:

1. A surgical tool having an electromagnetic (EM) sensor component, the surgical tool comprising:
   a flexible shaft portion; and
   a rigid portion attached to the flexible shaft portion,
   wherein the rigid portion comprises at least one EM sensor within the rigid portion,
   wherein the at least one EM sensor comprises an extended core portion surrounded by a coil,
   wherein the at least one EM sensor extends along a majority of a length of the rigid portion,
   wherein the coil extends along only a portion of a length of the extended core portion, and
   wherein the at least one EM sensor generates a change in voltage when exposed to an electromagnetic field.

2. The surgical tool of claim 1, wherein the surgical tool is an endoscope.

3. The surgical tool of claim 1, wherein the rigid portion is a tip of the surgical tool.

4. The surgical tool of claim 1, wherein the at least one EM sensor has an internally extending core.

5. The surgical tool of claim 4, wherein the surgical tool is an endoscope.

6. The surgical tool of claim 1, wherein the at least one EM sensor has an externally extending core.

7. The surgical tool of claim 6, wherein the externally extending core comprises a force sensing component.

8. The surgical tool of claim 7, wherein the force sensing component has a spherical shape.

9. The surgical tool of claim 1, wherein the at least one EM sensor has a diameter of approximately 300 μm.

10. The surgical tool of claim 1, wherein the at least one EM sensor has ferrous core.

11. A surgical tool having an electromagnetic (EM) sensor component, the surgical tool comprising:
    a flexible shaft portion; and
    a rigid portion attached to the flexible shaft portion,
    wherein the rigid portion comprises two EM sensors within the rigid portion,
    wherein at least one EM sensor of the two EM sensors comprises an extended core portion surrounded by a coil,
    wherein the coil of the at least one EM sensor extends along less than a full length of the extended core portion, and
    wherein the at least one EM sensor extends along a majority of a length of the rigid portion.

12. The surgical tool of claim 11, wherein the two EM sensors are positioned obliquely with respect to each other.

13. The surgical tool of claim 11, wherein the two EM sensors are positioned parallel with respect to each other.

14. The surgical tool of claim 11, wherein a first EM sensor of two EM sensors comprises an externally extended core portion and wherein a second EM sensor of the two EM sensors does not have an extended core portion.

15. The surgical tool of claim 11, wherein a first EM sensor of two EM sensors comprises an internally extended core portion and wherein a second EM sensor of the two EM sensors does not have an extended core portion.

16. The surgical tool of claim 11, wherein a first EM sensor of two EM sensors comprises an externally extended core portion and wherein a second EM sensor of the two EM sensors comprises an internally extended core portion.

17. The surgical tool of claim 11, wherein at least one EM sensor of the two EM sensors generates a change in voltage when exposed to an electromagnetic field.

18. A surgical tool, comprising:
    a flexible portion forming a part of a shaft of an endoscope, wherein the flexible portion is configured to operably connect to a robotic arm;
    a rigid portion attached to the flexible shaft portion, wherein the rigid portion forms a tip of the endoscope;
    a camera in the tip of the endoscope;
    at least one illumination component in the tip of the endoscope;
    a working channel in the tip of the endoscope; and
    at least one electromagnetic (EM) sensor in the tip of the endoscope,
    wherein the at least one EM sensor is configured to be used to spatially track the tip of the endoscope,
    wherein the at least one EM sensor extends along a majority of a length of the tip,
    wherein the at least one EM sensor is configured to generate a change in voltage when exposed to an electromagnetic field,
    wherein the at least one EM sensor comprises a core surrounded by a coil, and
    wherein the core but not the coil of the at least one EM sensor extends from the rigid portion into the flexible portion.

19. The surgical tool of claim 18, wherein the at least one illumination component comprises two illumination components on opposite sides of the camera.

20. The surgical tool of claim 18, wherein the at least one EM sensor comprises two EM sensors on opposite sides of the camera.

21. The surgical tool of claim 18, wherein the at least one EM sensor comprises two EM sensors positioned at non-parallel angles with respect to each other.

22. (Previously Pending) The surgical tool of claim 18, wherein the at least one EM sensor comprises a single EM sensor that partially overlaps a central axis of the tip.

23. A surgical tool, comprising:
    a shaft;

a tip attached to the shaft;
at least one illumination component in the tip;
a working channel in the tip;
a first electromagnetic (EM) sensor comprising a first core and a first coil at least partially surrounding the first core, wherein the first core is partially within the tip and partially within the shaft, and wherein the first EM sensor extends along a majority of a length of the tip; and
a second EM sensor comprising a second core and a second coil at least partially surrounding the second core, wherein the second core is partially within the tip and partially within the shaft, wherein the second EM sensor is positioned obliquely with respect to the first EM sensor, and wherein the second EM sensor extends along a majority of the length of the tip.

24. The surgical tool of claim 23, wherein the shaft is flexible and the tip is rigid.

25. The surgical tool of claim 23, further comprising a camera in the tip, wherein the at least one illumination component comprises a pair of fiber optics illumination sources on opposing sides of the camera.

26. The surgical tool of claim 23, wherein the surgical tool is an endoscope configured to be used in conjunction with a robotic arm to assist in surgery of a patient.

27. The surgical tool of claim 23, wherein each of the first and second coils is configured to induce a voltage when placed in an EM field, wherein each of the first and second EM sensors is configured to output voltage information related to a change in the electromagnetic field as the position and orientation of each of the first and second EM sensors changes.

* * * * *